(12) United States Patent
Gutierrez (10) Patent No.: US 7,474,916 B2
(45) Date of Patent: Jan. 6, 2009

(54) METHOD AND APPARATUS FOR DISCRIMINATING VENTRICULAR AND SUPRAVENTRICULAR TACHYARRHYTHMIAS

(75) Inventor: German Gutierrez, Madrid (ES)

(73) Assignee: Medtronic, Inc., Minneapolis, MN (US)

( * ) Notice: Subject to any disclaimer, the term of this patent is extended or adjusted under 35 U.S.C. 154(b) by 404 days.

(21) Appl. No.: 11/321,185

(22) Filed: Dec. 29, 2005

(65) Prior Publication Data
US 2006/0247703 A1 Nov. 2, 2006

Related U.S. Application Data

(60) Provisional application No. 60/675,833, filed on Apr. 28, 2005.

(51) Int. Cl.
*A61B 5/046* (2006.01)
(52) U.S. Cl. ..................................................... 600/518
(58) Field of Classification Search .................. 600/518
See application file for complete search history.

(56) References Cited

U.S. PATENT DOCUMENTS

| | | | |
|---|---|---|---|
| 5,193,535 A | 3/1993 | Bardy et al. | |
| 5,342,402 A | 8/1994 | Olson et al. | |
| 5,447,519 A * | 9/1995 | Peterson | 607/5 |
| 5,545,186 A | 8/1996 | Olson et al. | |
| 6,308,095 B1 * | 10/2001 | Hsu et al. | 600/518 |
| 6,393,316 B1 | 5/2002 | Gillberg et al. | |
| 6,430,435 B1 | 8/2002 | Hsu et al. | |
| 6,490,478 B1 | 12/2002 | Zhang et al. | |
| 6,654,639 B1 * | 11/2003 | Lu | 607/17 |
| 2003/0074026 A1 | 4/2003 | Thompson et al. | |

\* cited by examiner

*Primary Examiner*—Kennedy J Schaetzle
(74) *Attorney, Agent, or Firm*—Michael C. Soldner (57) ABSTRACT

A system and method are provided for discriminating supraventricular tachycardia (SVT) from ventricular tachycardia (VT). A monitoring EGM signal is acquired during a sensing window timed according to the time of R-wave detection on a reference EGM signal. A normal sinus rhythm (NSR) template is generated using the monitoring EGM signal during the time-referenced sensing window. During an unknown rhythm, the monitoring EGM signal sensed during the time-referenced sensing window is compared to the NSR template for use in computing a morphology metric. The morphology metric is compared to a VT/VF detection threshold for discriminating SVT from VT/VF.

14 Claims, 8 Drawing Sheets

METHOD AND APPARATUS FOR DISCRIMINATING VENTRICULAR AND SUPRAVENTRICULAR TACHYARRHYTHMIAS

RELATED APPLICATION

The present application claims priority and other benefits from U.S. Provisional Patent Application Ser. No. 60/675,833, filed Apr. 28, 2005, entitled "METHOD AND APPARATUS FOR DISCRIMINATING VENTRICULAR AND SUPRAVENTRICULAR TACHYARRYTHMIAS", incorporated herein by reference in its entirety.

FIELD OF THE INVENTION

The present invention relates generally to the detection and treatment of arrhythmias in a medical device and, in particular, to an apparatus and method for discriminating ventricular tachycardia from supraventricular tachycardia.

BACKGROUND OF THE INVENTION

Implantable medical devices are available for treating cardiac arrhythmias by delivering electrical shock therapy for cardioverting or defibrillating the heart in addition to cardiac pacing. Such a device, commonly known as an implantable cardioverter defibrillator or "ICD", senses a patient's heart rhythm and classifies the rhythm according to an arrhythmia detection scheme in order to detect episodes of tachycardia or fibrillation. Single chamber devices are available for treating ventricular arrhythmias, and dual chamber devices are available for treating both atrial and ventricular arrhythmias. Arrhythmias detected may include ventricular tachycardia (VT), fast ventricular tachycardia (FVT), ventricular fibrillation (VF), atrial tachycardia (AT) and atrial fibrillation (AF).

Upon detecting an arrhythmia, the ICD delivers an appropriate therapy. Cardiac pacing is delivered in response to the absence of sensed intrinsic depolarizations, referred to as P-waves in the atrium and R-waves in the ventricle. In response to tachycardia detection, a number of tiered therapies may be delivered beginning with anti-tachycardia pacing therapies and escalating to more aggressive shock therapies until the tachycardia is terminated. Termination of a tachycardia is commonly referred to as "cardioversion." Ventricular fibrillation (VF) is a serious life-threatening condition and is normally treated by immediately delivering high-energy shock therapy. Termination of VF is normally referred to as "defibrillation."

In modern implantable cardioverter defibrillators, the physician programs the particular anti-arrhythmia therapies into the device ahead of time, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected.

Reliable ICD performance depends on accurate detection and discrimination of arrhythmias. A delivered therapy is generally painful to the patient and depletes the battery charge. Inappropriately delivered therapies can induce arrhythmias in some patients. It is desirable, therefore, to avoid delivering a therapy due to inappropriate arrhythmia detection. For example, it is undesirable to deliver cardioversion therapy during normal, sinus tachycardia that is a heart rate increase in response to exercise. Supraventricular tachycardias (SVT), which may be atrial tachycardia, atrial flutter, or atrial fibrillation, may be conducted to the ventricles and detected as ventricular tachycardia (VT) or ventricular fibrillation (VF), resulting in the delivery of a ventricular cardioversion or defibrillation therapy when no ventricular therapy is needed.

One approach to detecting arrhythmias is based on monitoring sensed event intervals. Monitoring of sensed intervals generally involves identifying the event intervals and event rates as they occur and applying a preset group of criteria which must be met in order to detect a particular arrhythmia. Criteria for identifying various arrhythmias may all be monitored simultaneously. An arrhythmia detection and classification system generally disclosed in U.S. Pat. No. 5,342,402, issued to Olson et al., incorporated herein by reference in its entirety, uses criteria for sensed events, event intervals, and event rates.

Certain arrhythmias may be difficult to detect based on event intervals alone. Some patients may experience ventricular tachycardia and ventricular fibrillation having similar rates or varying rates. In other cases, a high ventricular rate may in fact be due to a supraventricular arrhythmia. Criteria for arrhythmia detection may overlap. An example of an arrhythmia detection and classification system that employs a prioritized set of inter-related rules for arrhythmia detection is generally disclosed in U.S. Pat. No. 5,545,186, issued to Olson et al., incorporated herein by reference in its entirety. The highest priority rule that is satisfied at a given time controls the behavior of the device in regard to the delivery or withholding of therapy. This methodology includes classification of sensed events into a limited number of event patterns. Certain sequences of event patterns are strongly indicative of specific types of heart rhythms. This interval-based algorithm generally achieves high specificity in discriminating ventricular and supraventricular arrhythmias while maintaining high sensitivity to detecting ventricular arrhythmias overall. In order to improve the specificity of the arrhythmia classification, specific criteria were developed for effectively identifying the likely occurrence of supraventricular tachycardias and for identifying the likelihood that events sensed in the atrium are in fact far field R-waves rather than P-waves.

However, there are some arrhythmias that are known to cause detection challenges for interval based detection algorithms. Certain types of supraventricular tachycardias (SVTs) producing ventricular rates in the VT/VF detection zones may potentially be detected as VT or VF. One rhythm that may be inappropriately detected as VT according to interval-based detection schemes is atrial fibrillation that is rapidly conducted to the ventricles. This SVT may be detected as a double tachycardia (simultaneous ventricular and atrial tachycardia) resulting in delivery of a VT therapy.

Another example is ventricular tachycardia with long 1:1 retrograde conduction to the atria resulting in relatively regular P-R intervals that resemble a sinus tachycardia rhythm. In this case, the ventricular tachycardia may go undetected and VT therapy may be inappropriately withheld. In the reverse situation, sinus tachycardia or atrial tachycardia with long PR intervals may resemble ventricular tachycardia with 1:1 retrograde conduction, potentially resulting in inappropriate VT detection and unneeded delivery of VT therapy.

During AV nodal re-entrant tachycardia, nearly simultaneous P and R sensing may occur. When atrial sensed events occur sometimes before and sometimes after the ventricular sensed event, this rhythm might cause inappropriate VT detection. Simultaneous atrial fibrillation and polymorphic VT may have a P and R interval similar to rapidly conducted AF. Thus, this rhythm may be inappropriately classified as an SVT causing the polymorphic VT to go undetected.

An alternative approach to interval-based arrhythmia detection relies on EGM morphology analysis to discriminate a normal EGM morphology from an abnormal EGM morphology. U.S. Pat. No. 6,393,316, issued to Gillberg et al., incorporated herein by reference in its entirety, generally discloses a method and apparatus that uses a wavelet transform to discriminate normal and aberrantly conducted depolarizations. Discrimination of QRS complexes during ventricular tachycardia from normal QRS complexes during supraventricular tachycardia may be achieved using an EGM morphology analysis. Wavelet transform analysis, as well as other morphology analysis methods, generally require greater processing time and power than interval-based detection methods. Accuracy of morphology-based detection algorithms alone may be limited due to myopotential noise, low amplitude EGM signals, waveform alignment error, and rate-dependent aberrancy. Therefore, wavelet transform analysis has been combined with detection interval criteria such that a wavelet transform is performed upon detection of a fast rate.

In single chamber devices, an atrial signal is unavailable making the task of discriminating SVT from VT even more challenging since atrial rate information and P-R intervals and event patterns are not available. Ventricular EGM morphology information has been used in single chamber devices for providing improved specificity of SVT and VT detection. In particular, a detection algorithm using EGM width criterion which evaluates the width of the QRS complex during an unknown rhythm relative to the QRS width measured during known normal sinus rhythm. Clinical use of such algorithms has shown some improvement over rate-based detection algorithms however the specificity of VT detection generally remains around 80%.

It is recognized, therefore, that an improved system and methodology is desired to address challenges in arrhythmia detection, particularly in systems lacking an atrial EGM signal. In particular, a method is needed for improving the specificity of SVT discrimination without compromising the sensitivity for detecting VT and VF.

BRIEF DESCRIPTION OF THE DRAWINGS

Aspects and features of the present invention will be readily appreciated as the same becomes better understood by reference to the following detailed description when considered in connection with the accompanying drawings, wherein.

DETAILED DESCRIPTION

The present invention provides a system and method for detecting and discriminating VT/VF from SVT using morphology information derived from two unique ventricular EGM signals. Since both normal sinus rhythm (NSR) and SVT originate in the atria and are conducted to the ventricles via the A-V node, the morphology of the R-wave complex during NSR and SVT will generally be highly correlated. VT/VF originates in the ventricles and will generally present a change in the R-wave morphology, but not in all cases. The time difference between the R-wave peaks detected on a monitoring EGM signal and-on a-reference EGM signal during NSR is expected to change during VT/VF due to a change in the ventricular conduction pattern.

The system according to an embodiment of the present invention includes a reference EGM signal source and two unique monitoring EGM signal sources coupled to signal processing circuitry and a microprocessor with associated memory for analyzing and comparing the EGM signals for discrimination of VT/VF from SVT. In one embodiment, the reference EGM signal source and one monitoring EGM signal source are provided using the same sensing electrode configuration, and the second monitoring EGM signal source is provided using a different sensing electrode configuration. In other embodiments, each of the reference EGM signal source and two monitoring EGM signal sources are unique. In one embodiment, the reference EGM signal source is a bipolar EGM signal obtained between ventricular pace and sense electrodes. The two monitoring EGM signal sources are any other EGM sensing configurations available which can include sensing between any cardiac pacing, sensing, or high-voltage coil electrodes, the device housing or "CAN" electrode, and/or any other cardiac or subcutaneous electrodes available. In an exemplary embodiment, the present invention is implemented in an ICD coupled to one or more cardiac leads carrying electrodes for obtaining the reference and monitoring EGM signals. The ICD further includes timing and control circuitry and therapy delivery circuitry for providing an appropriate response to a detection of VT/VF or SVT based on EGM signal analysis.

According to an embodiment of the present invention, NSR templates are generated and stored in memory and used during cardiac rhythm monitoring for discriminating between VT/VF and SVT. To generate NSR templates, a series of EGM signals are acquired from successive cardiac cycles during a timing window applied to each of the monitoring EGM signal sources during confirmed NSR. The reference EGM signal is used to set the temporal location of the timing window during which the monitoring EGM signals are acquired. The timing window is centered at the time an R-wave fiducial point detection is made from the reference EGM signal. The series of acquired signals are used to generate respective NSR EGM templates for each of the monitoring EGM signal sources.

After obtaining NSR templates, arrhythmia monitoring can be performed during which morphology templates of the monitoring EGM signals are acquired during an unknown fast rhythm and compared to the NSR templates generated for the same monitoring EGM signal source. In one embodiment, morphological template comparisons include determining a correlation coefficient of the NSR template and the template for the unknown rhythm for each of the respective monitoring EGM signal sources. In another embodiment, the template comparisons include measuring a change in the time shift between the reference EGM R-wave detection and a monitoring EGM R-wave detection.

Figure 1:
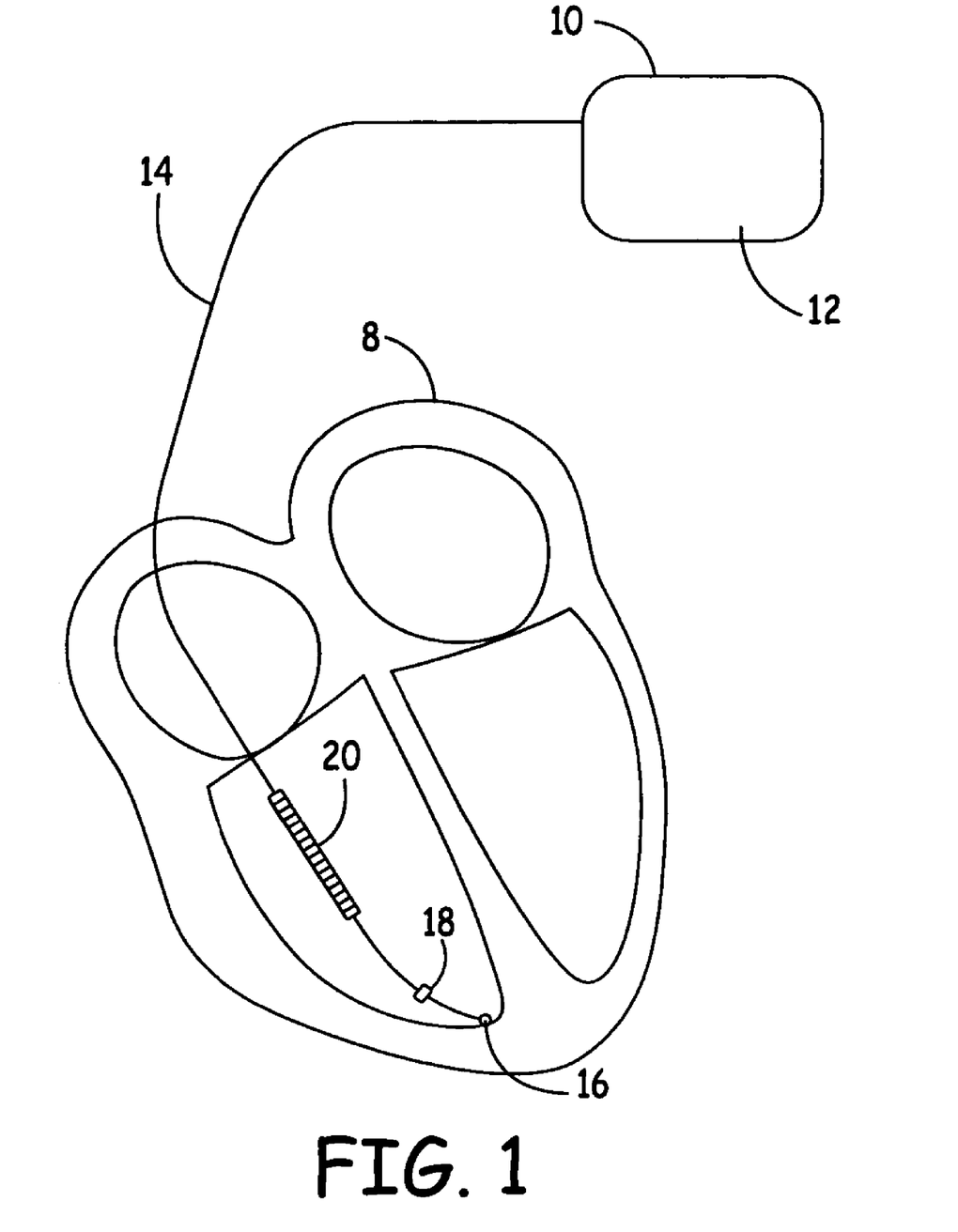
FIG. 1 is a schematic diagram of a medical device according to an embodiment of the present invention coupled to a patient's heart via a cardiac lead.

A VT/VF detection requirement is defined for discriminating between SVT and VT/VF based on a morphology metric determined from the template comparisons. One or more morphology metrics are determined from the template comparisons. If an interval-based VT/VF measurement satisfies a VT/VF detection requirement, detection of VT/VF is made based on the subsequent satisfaction of the morphology metric requirement. If the VT/VF morphology detection requirement is not satisfied, SVT is detected. A suitable therapy response may be provided based on the VT/VF or SVT detection FIG. 1 is a schematic diagram of a medical device 10 coupled to a patient's heart 8 via a cardiac lead 14, according to an embodiment of the present invention. Lead 14 is provided as an endocardial pacing and cardioversion lead and is shown deployed in the right ventricle of heart 8. Lead 14 is equipped with a tip electrode 16 and ring electrode 18 used for delivering bipolar pacing pulses to heart 8 and for bipolar sensing of cardiac EGM signals. Lead 14 further includes a high-voltage coil electrode 20 for use in delivering high-voltage cardioversion and defibrillation therapies to heart 8 upon detection of arrhythmias based on sensed EGM signals. In the particular configuration shown, device housing 12 can be used as a "CAN" or "case" electrode in conjunction with coil electrode 20 for delivering high-voltage therapies. Device 10 shown here is embodied as a single chamber ICD used for sensing ventricular signals in the right ventricle and for responding to sensed signals by delivering pacing, cardioversion, or defibrillation therapies as needed in the right ventricle The methods provided by the present invention are particularly beneficial in a single-chamber ICD of the type shown in FIG. 1 in that VT/VF can be discriminated from SVT without requiring any additional leads or electrodes for sensing atrial signals. However, even in dual chamber devices where there is an atrial EGM signal available, discrimination of VT/VF from SVT can sometimes be problematic. As such, the present invention may be incorporated into any single, dual or multi-chamber device to improve the specificity of arrhythmia detection algorithms.

As will be described in detail below, VT/VF and SVT are discriminated based on a morphological analysis of two monitoring EGM signals using a reference EGM signal for timing a sensing window during which the monitoring EGM signals are acquired. Discrimination of SVT from VT/VF with high specificity while maintaining high sensitivity to VT/VF detection will improve the performance of device 10 by reducing the likelihood of delivering unnecessary VT or VF therapies due to inappropriate detection of an SVT as VT or VF.

With regard to the configuration shown in FIG. 1, a reference EGM signal may be sensed using the bipolar combination of tip electrode 16 and ring electrode 18. Monitoring EGM signals are selected as any two unique sensing configurations available from the electrodes provided. In one embodiment, one monitoring EGM sensing configuration is selected as the same as the reference EGM sensing configuration. For example, the reference EGM signal and one monitoring EGM signal may be selected as the bipolar tip electrode 16 to ring electrode 18 configuration and the second monitoring EGM signal may be selected as any other sensing configuration, such as: coil electrode 20 to CAN electrode 12; tip electrode 16 to CAN electrode 12; ring electrode 18 to CAN electrode 12; tip electrode 16 to coil electrode 20; or ring electrode 18 to coil electrode 20.

It is recognized that the present invention may be implemented in numerous types of implantable devices having varying lead and electrode configurations. Practice of the invention is therefore not limited to the illustrated embodiment shown in FIG. 1. The invention may be implemented in any single chamber, dual-chamber, or multi-chamber cardiac stimulation device, drug delivery device, or monitoring-only device that is coupled to a set of cardiac and/or subcutaneous electrodes wherein at least two unique ventricular EGM sensing configurations are available. Electrodes may include intravenous electrodes, endocardial electrodes, epicardial electrodes, and/or subcutaneous or submuscular electrodes. The present invention will benefit any monitoring or therapy delivery device functions that rely on accurate detection and discrimination of VT/VF and SVT.

Figure 2:
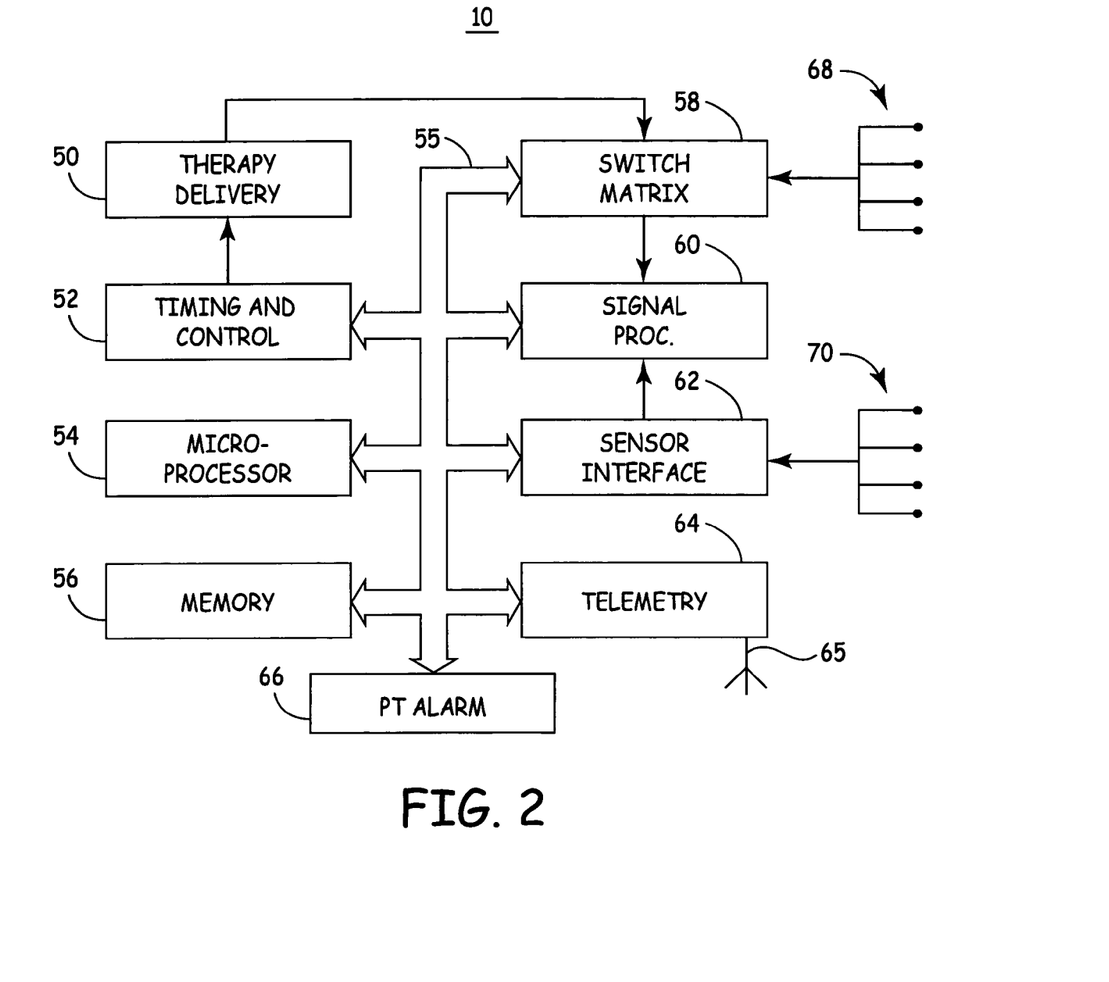
FIG. 2 is a block diagram of typical functional components of the medical device of FIG. 1.

FIG. 2 is a block diagram of typical functional components of a medical device, such as device 10 shown in FIG. 1. Device 10 generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of device 10 via a data/address bus 55. Device 10 may include therapy delivery unit 50 for delivering a therapy, such as an electrical stimulation or drug therapy, under the control of timing and control 52. In the case of electrical stimulation therapies, such as cardiac or neurostimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 are also used for sensing cardiac EGM signals and may be used for sensing other electrical signals within the body, such as cardiac impedance signals. In the case of cardiac stimulation devices, EGM signals are sensed for determining when an electrical stimulation therapy is needed and in controlling the timing of stimulation pulses. In accordance with the present invention, at least two unique EGM sensing configurations are selected from electrodes 68 using switch matrix 58 for use in VT/VF and SVT discrimination using the methods described below.

Electrodes 68 selected for sensing EGM signals are coupled to signal processing circuitry 60 via switch matrix 58. Signal processor 60 includes sense amplifiers and may include other signal conditioning circuitry, such as filters, and an analog to digital converter. Electrical signals may then be used by microprocessor 54 for detecting physiological events, such as detecting and discriminating cardiac arrhythmias. In particular, two monitoring EGM signals and one reference EGM signal are selected from electrodes 68 using switch matrix 58 for performing signal morphology analysis for discriminating VT/VF from SVT. In some embodiments, cardiac arrhythmia detection may be classified as a patient alert condition, which would cause device 10 to issue a patient alert signal using patient alarm circuitry 66.

Device 10 may additionally be coupled to one or more physiological sensors 70. Such sensors may include pressure sensors, accelerometers, flow sensors, blood chemistry sensors, activity sensors or other physiological sensors known for use with medical devices. Sensors 70 are coupled to device 10 via a sensor interface 62 which provides sensor signals to signal processing circuitry 60. Sensor signals are used by microprocessor 54 for detecting physiological events or conditions. For example, device 10 may monitor heart wall motion, blood pressure, blood chemistry, respiration, or patient activity. Monitored signals may be used for sensing the need for delivering a therapy under control of the operating system.

The operating system includes associated memory 56 for storing a variety of programmed operating mode and parameter values that are used by microprocessor 54. The memory 56 may also be used for storing data compiled from sensed physiological signals and/or relating to device operating history for telemetry out on receipt of a retrieval or interrogation instruction. All of these functions and operations are known in the art, and many are generally employed to store operating commands and data for controlling device operation and for later retrieval to diagnose device function or patient condition. In accordance with the present invention, EGM morphology templates acquired during NSR are stored in memory 56 and used by microprocessor 54 in discriminating VT/VF and SVT. Discrimination criteria defining VT/VF detection requirements and SVT detection requirements are also stored in memory 56.

Device 10 further includes telemetry circuitry 64 and antenna 65. Programming commands or data are transmitted during uplink or downlink telemetry between device telemetry circuitry 64 and external telemetry circuitry included in a programmer or monitoring unit. Telemetry circuitry 64 and antenna 65 may correspond to telemetry systems known in the art.

Device 10 may optionally be equipped with patient alarm circuitry 66 for generating audible tones, a perceptible vibration, muscle stimulation or other sensory stimulation for notifying the patient that a patient alert condition has been detected by device 10. A patient alert condition may be the detection of an arrhythmia or notification of an impending defibrillation shock.

Figure 3A:
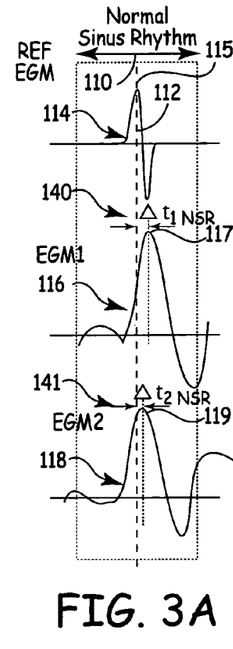
FIGS. 3A through 3D are graphical illustrations of a reference EGM signal (REF EGM), and two monitoring EGM signals (EGM1 and EGM2) recorded during known rhythms corresponding to NSR (FIG. 3A), SVT (FIG. 3B) and two different episodes of VT, VT1 (FIG. 3C) and VT2 (FIG. 3D).
Figures 3B, 3C, 3D:
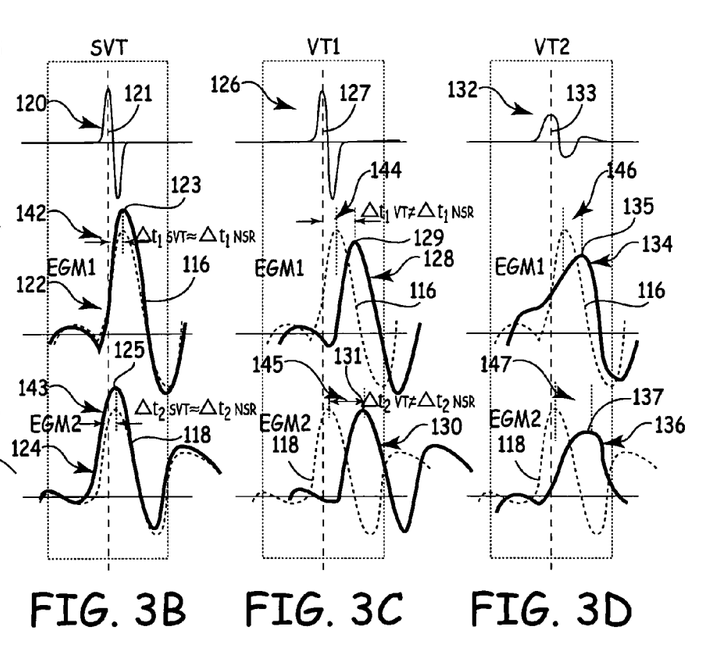

FIGS. 3A through 3D are graphical illustrations of a reference EGM signal (REF EGM), and two monitoring EGM signals (EGM1 and EGM2) recorded during known rhythms corresponding respectively to NSR (FIG. 3A), SVT (FIG. 3B) and two different episodes of VT, VT1 (FIG. 3C) and VT2 (FIG. 3D). These examples demonstrate the use of two monitoring EGM signals time-referenced to a reference EGM signal for discriminating VT/VF from SVT. As will be described, the examples show that the R-wave morphology may or may not change during VT. However, the time of an R-wave peak during VT will change relative to R-wave peaks occurring on other EGM signals due to changes in the ventricular conduction pattern during VT/VF. The use of time-referenced monitoring EGM signals allows both morphology and depolarization time-shift information to be recognized as evidence of an altered ventricular conduction pattern associated with ventricular arrhythmia.

Referring to FIG. 3A, the reference EGM signal 114 and monitoring EGM signals 116 and 118 are obtained during a sensing window 110. Sensing window 110 is referenced in time to an event detection made on the reference EGM 114. In an exemplary embodiment, the timing of sensing window 110 is based on R-wave detection 112. In the examples shown, sensing window 110 is shown centered at the time of R-wave detection 112. The sensing window duration is predefined and may be, for example, approximately 200 ms.

In these examples, R-wave detection coincides with the R-wave peak. In other embodiments, other features of the reference EGM signal 102 can be used for time-referencing the sensing window 110, such as a threshold crossing, a peak derivative, or other selected fiducial point. Sensing window 110 can be time-referenced to any designated reference EGM fiducial point and defined in any way relative to the fiducial point, such as starting at a given offset from the fiducial point, extending a predetermined amount of time in either direction from the fiducial point, etc. In the exemplary embodiments described herein, the sensing window applied to the monitoring EGM1 and EGM2 signals is centered at the time of the R-wave peak of the reference EGM.

During NSR, the R-wave peak 117 of the monitoring EGM1 signal 116 is shifted in time, $\Delta t_1(NSR)$ 140, relative to the time of R-wave detection 112 on the reference EGM signal 114. Likewise, the R-wave peak 119 of the monitoring EGM2 signal 118 is shifted in time, $\Delta t_2(NSR)$ 141, relative to the time of R-wave detection 112 made on the reference EGM signal 114. The time shifts $\Delta t_1(NSR)$ 140 and $\Delta t_2(NSR)$ 141 relate to the normal propagation of the ventricular depolarization as it travels through the ventricles. Changes in these time shifts are indicative of an altered ventricular conduction pattern such as during VT/VF.

In FIG. 3B, the reference EGM signal 120, monitoring EGM1 signal 122, and monitoring EGM2 signal 124 are shown during SVT. The morphology of monitoring EGM1 signal 122 during SVT is substantially equal to the morphology of the NSR EGM1 signal 116 (shown by dotted line). Furthermore, the time shift $\Delta t_1(SVT)$ 142 between R-wave peak 123 of monitoring EGM1 122 and the time of R-wave detection 121 on reference EGM 120 is substantially equal to the time shift $\Delta t_1(NSR)$ 140 during normal sinus rhythm. The similarity of the EGM1 morphology and R-wave time shifts during SVT and NSR are expected since both NSR and SVT originate in the atria and are conducted to the ventricles via the A-V node.

Likewise, the morphology of signal EGM2 124 during SVT is substantially equal to the morphology of the NSR EGM2 signal 118 (dotted line). The time shift $\Delta t_2(SVT)$ 143 between the R-wave peak 125 of monitoring EGM2 124 and the time of R-wave detection 121 on reference EGM 120 is substantially equal to the time shift $\Delta t_2(NSR)$ 141.

FIG. 3C shows the reference EGM signal 126, monitoring EGM1 signal 128 and monitoring EGM2 signal 130 during a VT episode referred to as VT1. During VT, which arises in the ventricles, the morphologies of the monitoring EGM1 and EGM2 signals might be substantially changed from the respective EGM1 and EGM2 NSR morphologies. However, it is possible that the monitoring EGM morphologies are substantially equal during NSR and during VT, but the time shift between R-wave detection on the reference EGM signal and a monitoring EGM signal is substantially changed due to an altered ventricular conduction pattern. As shown in FIG. 3C, the morphology of the VT1 EGM1 signal 128 is substantially equal to the morphology of the NSR EGM 1 signal 116 (shown by dotted line in FIG. 3C). However, the time shift $\Delta t_1(VT1)$ 144 between the R-wave peak 129 of VT1 EGM1 signal 128 is not equal to the time shift $\Delta t_1(NSR)$ 140. Likewise, the morphologies of the VT1 EGM 2 signal 131 and the NSR EGM2 signal 118 are substantially equal, but the time shift $\Delta t_2(VT1)$ 145 is not equal to the time shift $\Delta t_2(NSR)$ 141.

The changes in the time shifts between monitoring EGM1 and EGM2 R-wave peaks and the time of R-wave detection 125 on reference EGM 126 enable discrimination of this VT1 episode from SVT. A morphological analysis that compares only the morphology of the R-wave complex would not discriminate the monitoring EGM1 128 and EGM2 130 signals during a VT1 event from the corresponding monitoring EGM1 122 and EGM2 124 signals during SVT. By time-referencing the monitoring EGM sensing windows to the time 127 of R-wave detection on reference EGM 126, the change in R-wave peak time shifts $\Delta t_1(VT1)$ 144 and $\Delta t_2(VT1)$ 145 of the respective monitoring EGM1 and EGM2 signals can be recognized, even when the morphology of the signal features remain relatively unchanged. Despite the similarity of the morphology of the monitoring EGM signal waveforms during NSR and during VT1, a comparison of the time-referenced signals in accordance with the present invention will result in there being a low correlation between the VT1 EGM1 signal 128 and the NSR EGM1 signal 116 and a low correlation between the VT1 EGM2 signal 130 and the NSR EGM2 signal 118, indicating the likely presence of the VT1 event.

FIG. 3D shows reference EGM 132, monitoring EGM1 134 and monitoring EGM2 136 during a different VT episode referred to as VT2. The example recordings shown in FIG. 3D illustrate both the morphological change and the change in R-wave time shifts between unique EGM signals that can occur during VT. During this VT2 episode, the morphology of reference EGM 132, the monitoring EGM 1 134 and monitoring EGM 2 signal 136 are all substantially changed from the corresponding NSR signals. The morphology of NSR EGM1 116 and NSR EGM2 118 are shown by dotted lines in FIG. 3D for reference.

The time shift $\Delta t_1(VT2)$ 146 between EGM1 R-wave peak 135 and the time 133 of R-wave detection on reference EGM 132 is unequal to time shift $\Delta t_1(NSR)$ 140. The time shift $\Delta t_2(VT2)$ 147 between EGM2 R-wave peak 137 and the R-wave detection time 133 on reference EGM 132 is not equal to time shift $\Delta t_2(NSR)$ 141. Therefore, the present invention will determine that both the correlation of the VT2 EGM1 signal 134 and the NSR EGM1 signal 116 and the correlation of the VT2 EGM2 signal 136 and the NSR EGM2 signal 118 will be low, indicating the presence of a cardiac event other than a normal event, such as sinus rhythm or supraventricular tachycardia, for example.

In an exemplary embodiment, two unique monitoring EGM signals are used. It is possible during some abnormal ventricular rhythms that the correlation between one monitoring EGM signal and the corresponding NSR EGM signal will be high and the correlation between the second monitoring EGM signal and the corresponding NSR EGM signal is low. Hence, inclusion of two unique monitoring EGM signals will allow more reliable detection of changes in ventricular EGM signals associated with a rhythm arising from the ventricles rather than an SVT. However, it is possible, in some embodiments, to practice the invention using only one monitoring EGM signal time referenced to a reference EGM signal, though in some instances VT/VF may be inappropriately detected as an SVT. In other embodiments, more than two monitoring EGM signals, time-referenced to the reference EGM signal, may be selected.

Figure 4:
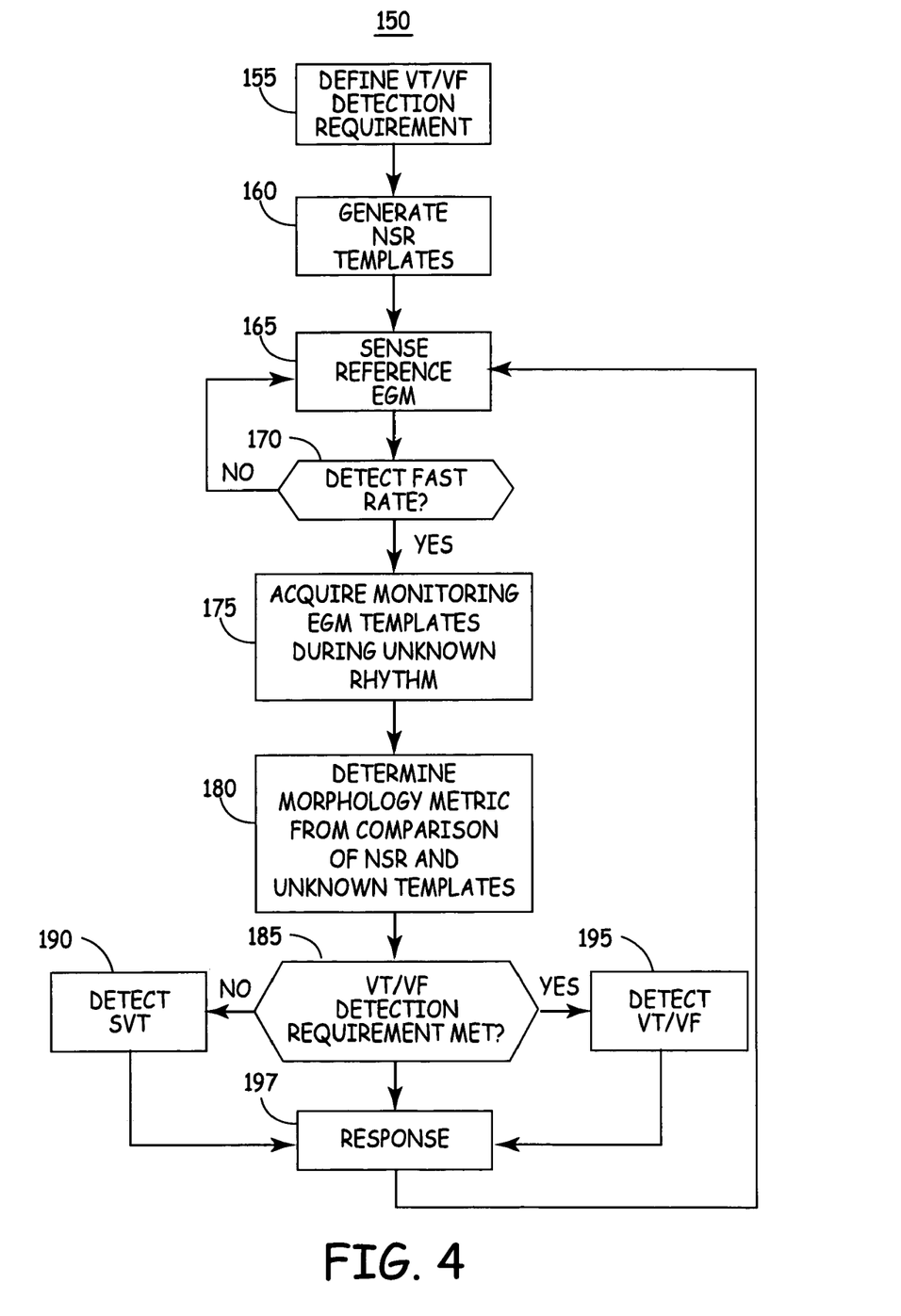
FIG. 4 is a flow chart of a method for discriminating VT/VF and SVT using time-referenced monitoring EGM signals according to an embodiment of the present invention.

FIG. 4 is a flow chart of a method for discriminating cardiac events using time-referenced monitoring EGM signals according to an embodiment of the present invention. At step 155, a VT/VF detection requirement is defined based on morphological comparisons of monitoring EGM signals acquired during an unknown rhythm to corresponding monitoring EGM morphology templates obtained during NSR, using the same sensing electrode configuration. As will be described in greater detail below, one or more morphology metrics will be determined for measuring the difference between the morphology of the monitoring EGM signals during an unknown rhythm and the morphologies of the corresponding monitoring EGM signals during NSR. A VT/VF detection requirement can be defined as a morphology metric threshold value that is indicative of at least one of the monitoring EGM signal morphologies during the unknown rhythm becoming substantially unequal to the corresponding NSR monitoring EGM signal morphology.

At step 160, NSR morphology templates are generated for each of the monitoring EGM signals. The generation of NSR templates will be described in greater detail in conjunction with FIG. 5.

At step 165, cardiac rhythm monitoring begins by sensing the reference EGM signal. The reference EGM signal is used to detect R-waves for determining R-R intervals for the detection of a high ventricular rate. The detection of a high ventricular rate can be based on a predetermined number of R-R intervals that fall within a tachycardia or fibrillation detection interval zone out. Such interval-based detection methods are known in the art. The reference EGM signal may be obtained from a ventricular tip-to-ring bipolar sensing configuration, as described previously, or from any other available sensing electrode configuration.

The EGM signal relied upon for detecting a fast ventricular rate is not required to be the same as the reference EGM signal used for time referencing monitoring EGM signals. Another EGM signal that is normally used by the implanted device for determining ventricular rate information can be used. Furthermore, other methods for detecting a fast ventricular rate could be used such as sensing other physiological signals including blood pressure signals, wall motion signals, heart sounds, blood oximetry signals, blood flow signals, or any other signal that contains ventricular cycle information for reliably determining the ventricular rate.

Upon detecting a fast rate, as determined at decision step 170, method 150 enables sensing of the monitoring EGM1 and EGM2 signals at step 175. EGM1 and EGM2 signal templates are generated from one or more cardiac cycles during the unknown, fast rhythm. The EGM1 and EGM2 signal templates are obtained during a sensing window that is applied during the cardiac cycle at a time relative to the R-wave detection made from the reference EGM signal. Depending on the capabilities of the device, the monitoring EGM1 and EGM2 signals may be acquired simultaneously, sequentially or in an alternating fashion.

At step 180, a comparison of the unknown monitoring EGM template acquired during the fast rate and the previously obtained NSR EGM template is made. In one embodiment, two monitoring EGM templates, EGM1 and EGM2, are acquired during the unknown rhythm and compared to respective NSR EGM1 and NSR EGM2 templates. Multiple EGM1 and EGM2 templates may be acquired and compared to the corresponding NSR templates. For example, a monitoring EGM template acquired during an unknown rhythm may be based on a single cardiac cycle. A sequence of monitoring EGM templates, each based on a single cardiac cycle, may then be compared to the NSR template.

A morphology metric is computed from the morphological comparisons made at step 180. In one embodiment, the morphology metric is computed using correlation coefficients computed from the NSR and unknown rhythm template comparisons. For example, a morphology metric, D, for discriminating VT/VF from SVT can be computed from the following equation:

$$D = ((1-\rho_1) \times 10)^2 + ((1-\rho_2) \times 10)^2$$

wherein $\rho_1$ is the correlation coefficient computed from the comparison of the unknown EGM1 template to the NSR EGM1 template, and $\rho_2$ is the correlation coefficient computed from the comparison of the unknown EGM2 template to the NSR EGM2 template. The correlation coefficients $\rho_1$ and $\rho_2$ will have values in the range of (−1 to +1). The morphology metric D will therefore have a value ranging from (0 to +800).

A threshold value for the morphology metric D will have been previously defined at step 155 for discriminating between VT/VF and SVT. During an SVT, the correlation between the NSR and unknown rhythm templates will be high for both EGM1 and EGM2 comparisons. The corresponding correlation coefficients $\rho_1$ and $\rho_2$ will approach 1 in value resulting in a morphology metric D approaching 0 in value according to the above equation. As such a very low value for the morphology metric D will be indicative of SVT.

During VT or VF, either or both of the correlation coefficients $\rho_1$ and $\rho_2$ will be low resulting in a relatively high value for the morphology metric D. A high value for D is therefore indicative of VT or VF. A threshold value for D is selected at step 155 such that a value greater than the threshold results in satisfaction of the VT/VF detection requirement at decision step 185, and VT/VF detection is made at step 195. If the morphology metric D is less than the threshold, the VT/VF detection requirement is not met as determined at decision step 185. SVT is detected at step 190.

The threshold value for D is selected such that satisfaction of the VT/VF detection requirement results in both a high sensitivity and high specificity for VT/VF detection. The threshold value may be selected as a nominal value or based on historical patient data or clinical data from a selected patient population. In one embodiment, a threshold value of 5 is selected, which is expected to provide high specificity of VT/VF detection without significantly affecting detection sensitivity.

Upon detection of SVT or VT/VF, an appropriate response to the detected rhythm can be provided at step 197. An appropriate response may be, but is not limited to, delivering a therapy, withholding a therapy, generating a report, or generating a patient alarm. After making the SVT or VT/VF detection and providing an appropriate response, method 150 returns to step 165 to continue monitoring the heart rhythm. The VT/VF detection requirement defined at step 155 and the NSR templates generated at step 160 can be updated any time by a clinician or may be updated automatically on a periodic basis.

In alternative embodiments, other morphology metrics may be derived or computed from EGM signal comparisons. As will be further described below, a morphology metric may be based on a measurement of the time shift between an R-wave feature on the monitoring EGM signal and the corresponding R-wave feature on the reference EGM signal. Other methods known in the art for performing morphological comparisons may be used for comparing a time-referenced monitoring EGM signal acquired during an unknown rhythm to a corresponding time-referenced monitoring EGM signal acquired during NSR.

Figure 5:
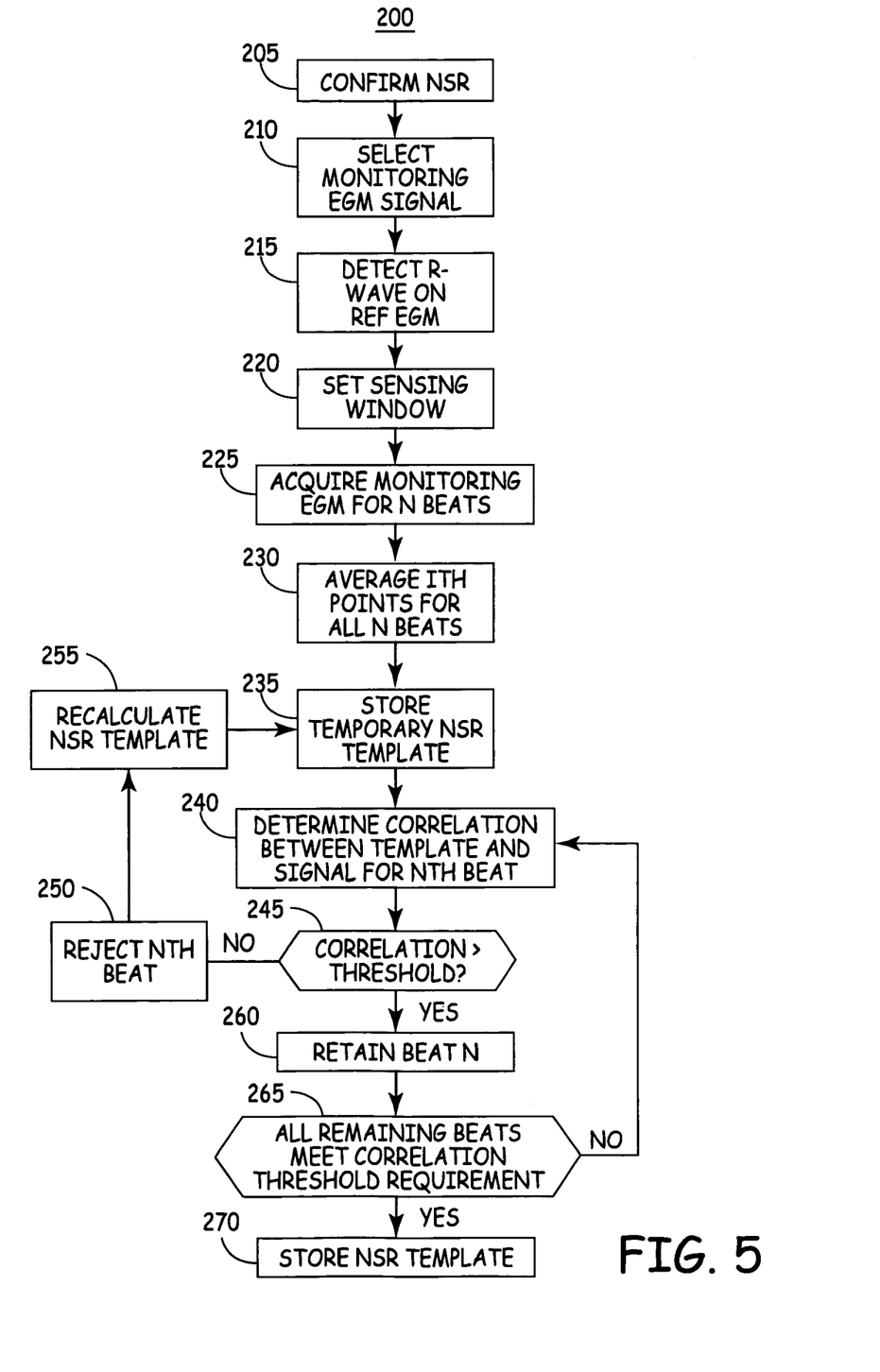
FIG. 5 is a flow chart of a method for generating a template of an EGM signal according to an embodiment of the present invention.

FIG. 5 is a flow chart summarizing steps included in a method for generating a template of an EGM signal according to an embodiment of the present invention. At step 205, the current rhythm is confirmed to be NSR. The templates generated using method 200 will be compared to monitoring EGM signals acquired during unknown rhythms used during cardiac rhythm monitoring as described above in conjunction with FIG. 4. In some embodiments, a template may be generated using method 200 during a known SVT rather than, or in addition to, during known NSR. An SVT template may then be compared to a monitoring EGM signal during an unknown rhythm for discriminating VT/VF from SVT. Multiple SVT templates may be generated for different types of known SVTs that a patient may commonly experience. However, one advantage of the present invention is that recognition of a rhythm that has originated in the atria and has been conducted to the ventricles can be achieved by evaluating two monitoring EGM signals time-referenced to a reference EGM signal without requiring multiple templates for each known SVT. Discrimination of VT/VF from SVT relies on the assumption that any rhythm originating in the atria will produce substantially equal monitoring EGM signal morphologies and R-wave time shifts between monitoring EGM signals and the reference EGM signal.

At step 210, a monitoring EGM signal is selected for generating a NSR template. Method 200 is repeated for each monitoring EGM signal to be used. Depending on device capabilities for sensing multiple EGM signals simultaneously, all or parts of method 200 may be performed contemporaneously for each of the monitoring EGM signals.

At step 215, R-wave detection from the reference EGM signal is performed to allow the monitoring EGM to be obtained during a sensing window that is time-referenced to the reference EGM. As described previously, the sensing window is set at step 220 based on the time of R-wave or other event detection made on the reference EGM. The monitoring EGM is obtained during the time-referenced sensing window for a desired number of cardiac cycles at step 225. In one embodiment, the sensing window is set relative to the time of reference EGM R-wave detection made on each cardiac cycle. For example, the sensing window is centered on the time of reference EGM R-wave detection.

The monitoring EGM is stored for one or more cardiac cycles, for example for 8 cardiac cycles, to allow an NSR template to be computed as an average of the stored signals. As such, at step 230 an average NSR monitoring EGM template is computed by averaging each ith point in the sensing window from each of the N cardiac cycles. The averaged EGM signal is stored as the temporary NSR template for the respective monitoring EGM at step 235.

At step 240, the monitoring EGM signal stored for each of the N cardiac cycles and used to compute the NSR template is compared to the temporary NSR template. If the correlation of the stored EGM signal to the temporary NSR template exceeds an acceptance threshold, as determined at decision step 240, the stored EGM signal is retained for computation of a permanent NSR template. If the correlation coefficient of the stored EGM signal and the temporary NSR template does not reach the acceptance threshold, the stored EGM signal is rejected at step 250. A new, averaged NSR signal template is computed at step 255 by averaging the stored EGM signals for the remaining N beats. The corrected NSR template is stored as the temporary NSR template at step 235.

The process of comparing each of the stored EGM signals for all N cardiac cycle repeats until the EGM signals for all remaining beats meet the correlation threshold requirement, as determined at decision step 265. The averaged signal of all stored EGM signals that meet the correlation requirement is stored as the NSR template for the corresponding monitoring EGM signal at step 270.

Method 200 is an iterative procedure for generating a NSR template representative of a corresponding monitoring EGM signal during NSR. Method 200 may also be used for generating monitoring EGM templates during an unknown rhythm. Alternative methods for generating a template for each of the monitoring EGM signals can be used. For example, other methods known in the art for rejecting anomalous beats can be used instead of comparisons of each stored EGM signal to a temporary NSR template. In some embodiments, a minimum number of cardiac cycles for generating an template may be required such that if too many beats are rejected, additional monitoring EGM signal samples need to be obtained.

Figure 6:
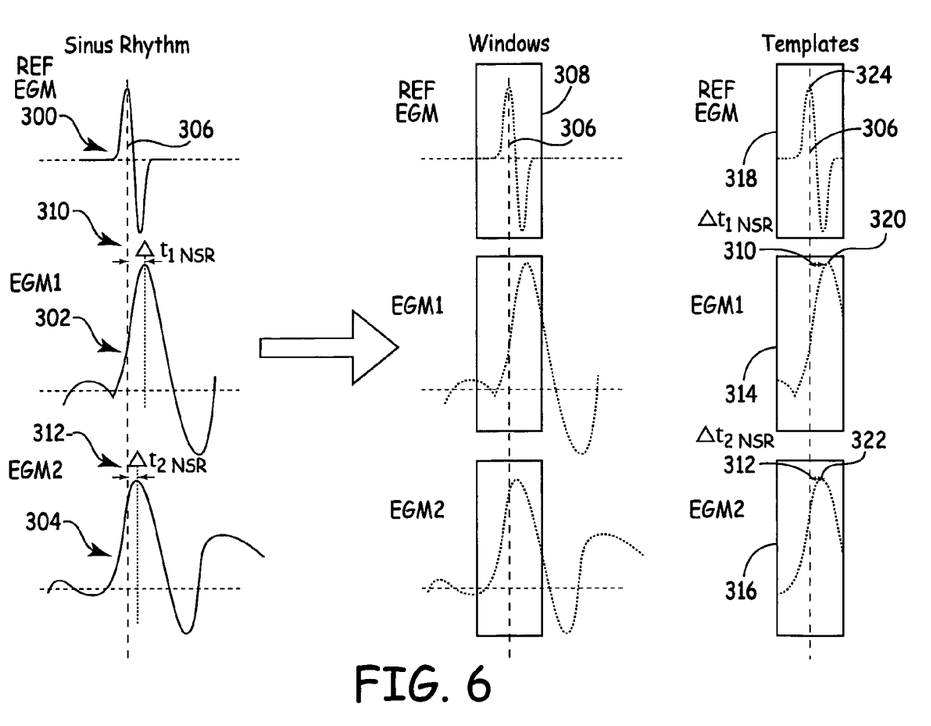
FIG. 6 are exemplary graphical illustrations of time-reference NSR signal templates according to an embodiment of the present invention.

FIG. 6 shows examples of time-reference NSR signal templates. During confirmed NSR, the reference EGM signal 300 is used for R-wave detection for time referencing the sensing window 308 during which the EGM1 302 and EGM2 304 signals are acquired. The time 306 of R-wave detection is used to set a sensing window 308 applied to monitoring EGM1 302 and monitoring EGM2 304. The timing of sensing window 308 is fixed relative to the reference EGM signal 300 and does not change relative to shifting of the R-wave peaks of the EGM1 302 and EGM2 304 signals. This aspect of the invention allows recognition of temporal changes in ventricular EGM signals relative to each other as a result of origination of the cardiac beat in the ventricles rather than in the atria.

In particular, changes in the time shift $\Delta t_1$ 310, between the monitoring EGM1 R-wave peak and the time 306 of R-wave detection on the reference EGM signal 300, and changes in the time shift $\Delta t_2$ 312, between the monitoring EGM2 R-wave peak and the time 306 of R-wave detection, which result from changes in the ventricular conduction pattern, can be recognized by fixing the sensing window 308 relative to the reference EGM 300. Only the EGM1 302 and EGM2 304 signal within the sensing window 308 is used for generating the respective NSR templates 314 and 316. The NSR templates 314 and 316 will contain both morphological information and time shift information. The complete R-wave complex for the monitoring EGM signals need not be encompassed by the sensing window 308.

According to an embodiment of the present invention, a NSR template 318 for the reference EGM signal 300 is also generated. A correlation coefficient may be determined for the reference EGM signal obtained during an unknown rhythm and the reference EGM NSR template 318. Since the sensing window is fixed relative to the time of R-wave detection, only changes in signal morphology will be detected.

The reference EGM NSR template 318 may alternatively be used to derive a morphology metric relating to the changes in the peak R-wave time shifts, $\Delta t_1$ 310 and $\Delta t_2$ 312. The time shifts $\Delta t_1$ 310 and $\Delta t_2$ 312 during NSR can be measured using the reference EGM NSR template 318 and the respective EGM1 NSR template 314 and EGM2 NSR template 316. During an unknown fast rhythm, the time shifts between R-wave detection on a reference EGM signal and the R-wave detection on the monitoring EGM signals can be measured. The time shifts measured during the unknown rhythm can be compared to the time shifts $\Delta t_1$ 310 and $\Delta t_2$ 312 measured during NSR. If both of the time shifts measured during an unknown rhythm are substantially equal to the corresponding NSR time shifts $\Delta t_1$ 310 and $\Delta t_2$ 312, the rhythm is detected as SVT. If either or both of the time shifts are not equal to the corresponding NSR time shifts $\Delta t_1$ 310 and $\Delta t_2$ 312, the unknown fast rhythm is detected as VT/VF.

Figure 7:
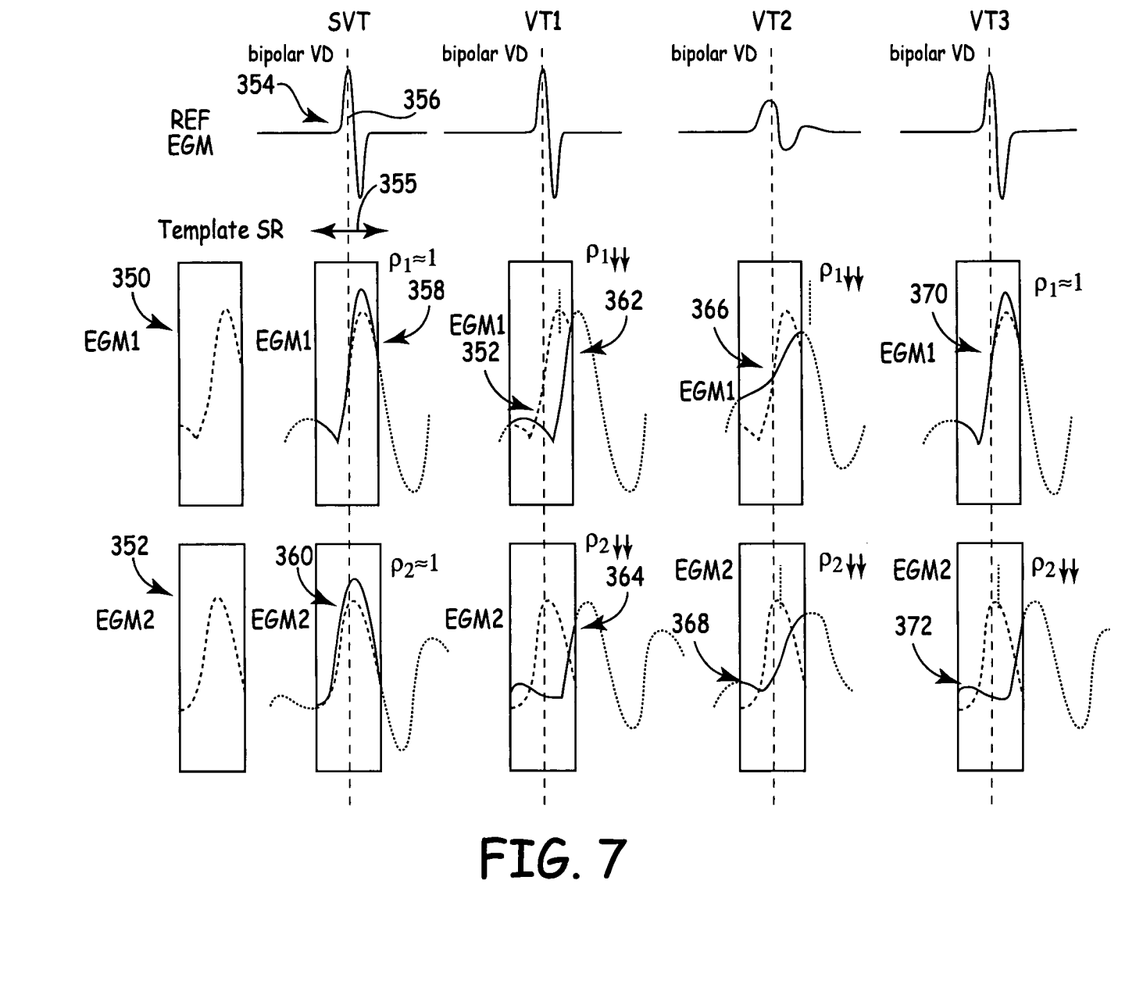
FIG. 7 exemplary graphical illustrations of monitoring EGM templates during a number of different rhythms according to an embodiment of the present invention.

FIG. 7 shows examples of monitoring EGM templates during a number of different rhythms, according to an embodiment of the present invention. The examples shown illustrate how evaluating the correlation of a monitoring EGM signal acquired during NSR and the monitoring EGM signal acquired during an unknown rhythm can be used to discriminate SVT from VT/VF. The templates acquired during a sensing window that is fixed relative to R-wave detection on the reference EGM signal allows both waveform morphology changes and time shifts of the R-wave complex that occur with or without waveform morphology changes to be recognized.

An NSR EGM1 template 350 and an NSR EGM2 template 352 are shown, which have been previously acquired during confirmed NSR. During SVT, the time of R-wave detection 356 on the reference EGM signal 354 is used to set a sensing window 355 during which monitoring EGM1 358 and monitoring EGM2 360 are captured. A comparative analysis of EGM1 358 during SVT and the NSR EGM1 template 350 results in a high correlation coefficient $\rho_1$, approaching or substantially equal to one. Likewise, EGM2 360 during SVT is highly correlated with the NSR EGM2 template 352. A morphology metric D defined according to the equation provide above would have a low value, below a VT/VF detection threshold, allowing an SVT detection to be made.

The remaining three examples of different VT episodes, VT1, VT2 and VT3, illustrate how changes in the EGM1 and EGM2 signals acquired during a sensing window referenced to the R-wave detection on the reference EGM signal provide evidence of VT/VF. The correlation coefficients, $\rho_1$ and $\rho_2$, computed from the comparisons of the VT1 EGM1 signal 362 to the NSR EGM1 signal 350 and the VT1 EGM2 signal 364 and the NSR EGM2 signal 352 will both be low due to a change in the time shifts of the R-waves relative to the reference EGM R-wave. The R-wave morphologies of the reference EGM, EGM1 and EGM2 are not substantially different than the corresponding R-wave morphologies during NSR. However, due to the change in time shifts between R-wave peaks, the morphology metric, D, defined by the equation above will have a high value, exceeding a VT/VF detection threshold.

In the second example of a VT episode, VT2, the morphology of the R-wave has changed for the reference EGM as well as monitoring EGM1 366 and monitoring EGM2 368. The correlation coefficients $\rho_1$ and $\rho_2$ will be low resulting in a high value for the morphology metric, D, which will exceed the threshold for VT/VF detection.

In the third example, the R-wave morphologies of the reference EGM signal, monitoring EGM1 370 and monitoring EGM2 372 are not substantially different than the corresponding R-wave morphologies during NSR. The time shift between the R-wave peak on EGM1 370 during VT3 and the reference EGM R-wave detection is substantially equal to the time shift observed between these signals during NSR. The correlation coefficient $\rho_1$ will approach a value of 1. However, the time shift between the R-wave peak on EGM2 372 during VT3 and the reference EGM signal has changed substantially from the time shift observed between these signals during NSR, indicating a change in ventricular conduction. As such, the correlation coefficient $\rho_2$ during VT3 will be low. The value of the morphology metric, D, will cross a VT/VF detection threshold due to the low correlation of the time-referenced VT3 EGM2 372 and NSR EGM2 352.

As seen by the illustrated examples of FIG. 7, SVT can be discriminated from VT/VF when both the relative time shifts of R-wave peaks occurring on different EGM signals and the morphologies of the R-waves are substantially equal to the R-wave morphologies and time shifts occurring during NSR, indicative of a rhythm originating in the atria. If either the time shifts between R-wave peaks change (as during VT1) or the morphology changes (as during VT2), VT/VF is detected. The time shift or morphology change may occur on only one of the monitoring EGM signals as illustrated by the example of VT3, still allowing a VT/VF detection to be made.

Figure 8:
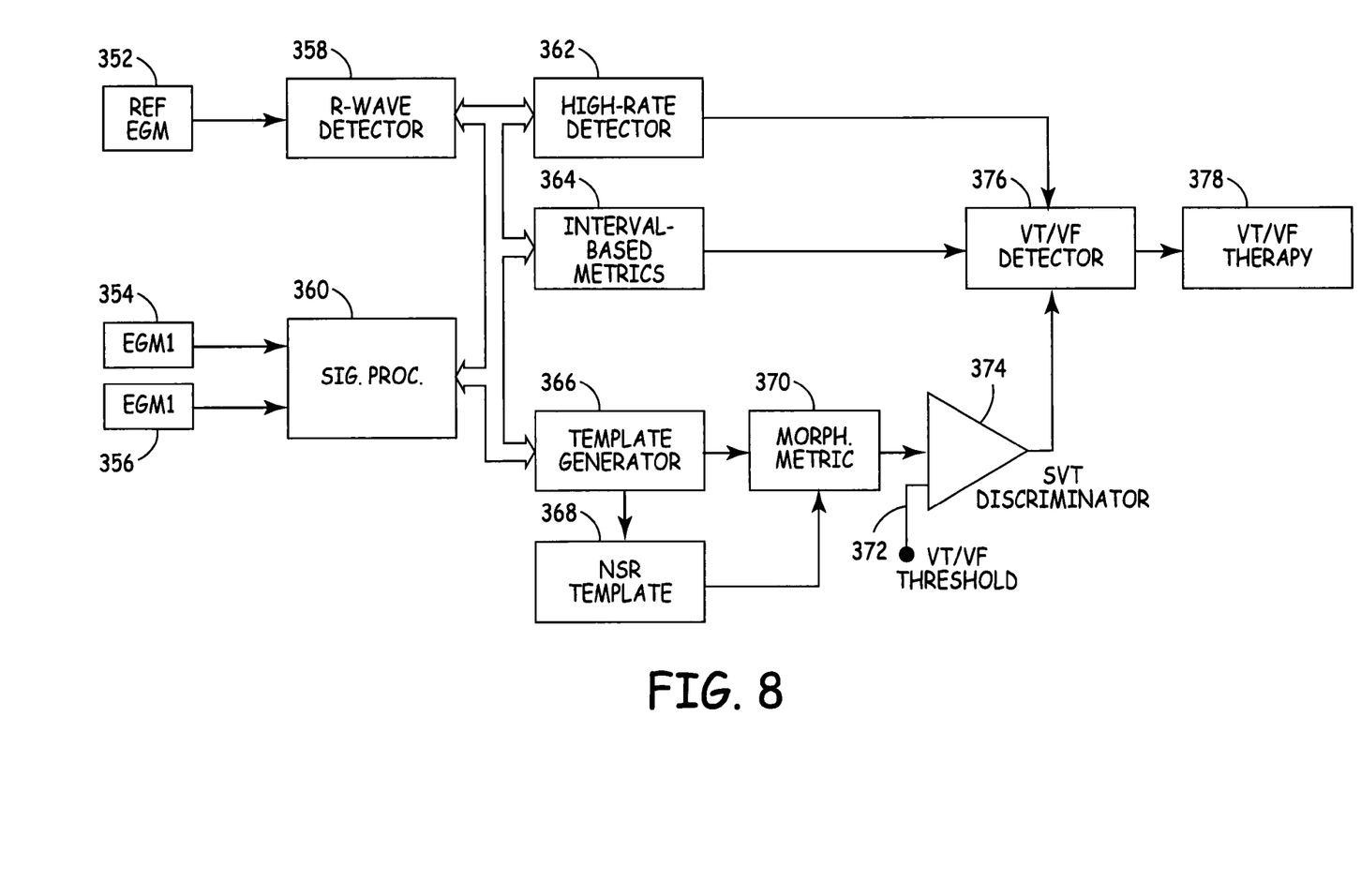
FIG. 8 is a functional block diagram of a medical device for utilizing a method for discriminating cardiac events according to an embodiment of the present invention.

FIG. 8 is a functional block diagram illustrating one implementation of the present invention in an ICD. A reference EGM signal 352 is provided as input to an R-wave detector 358 for use in determining the ventricular rate and detecting the presence of a high ventricular rate by high-rate detector 362. When a high rate is detected, interval based metrics of the ventricular rhythm can be determined by module 364. Interval based metrics may include rate stability and onset and can be used in combination with the rate information from high-rate detector 362 by VT/VF detector 376. Algorithms for detecting VT/VF using rate, stability and onset criteria are known in the art.

Detection of a high rate by high rate detector 362, enables sensing of monitoring EGM1 354 and EGM2 356, which are provided as input to signal processing circuitry 360, which includes suitable sense amplifiers, filters and analog-to-digital converters. Digitized EGM1 354 and EGM2 356 signals are provided to template generator 366 during a sensing window that is timed according to the time of an R-wave detection signal provided by R-wave detector 358.

EGM1 and EGM2 templates acquired during the fast rate are provided as input to module 370 for computing a morphology metric. Module 370 also receives previously stored NSR templates 368 as input. NSR templates 368 are created during NSR, when high-rate detector 362 is not detecting a high rate. During NSR, digital EGM1 and EGM2 signal output from signal processor 360 is provided as input to template generator 366 during sensing windows set relative to the time of R-wave detection signal output from R-wave detector 358. NSR templates 368 are derived from the time-referenced digital EGM1 and EGM2 signals acquired over a desired number of cardiac cycles. The NSR templates may be updated on a periodic basis when high-rate detector 362 is not detecting a high rate.

A morphology metric is computed by module 370 based on a comparative analysis of the EGM1 and EGM2 templates generated during the high rate and the respective stored NSR templates 368. The morphology metric is provided as input to comparator 374, which compares the metric to a VT/VF detection threshold 372. If the morphology metric crosses the VT/VF detection threshold 372, the SVT discriminator output of comparator 374 may be provided as "high" to VT/VF detector 376, providing a positive indication for VT/VF. If the morphology metric does not cross the VT/VF threshold, the SVT discriminator output of comparator 374 may be provided as "low" to VT/VF detector 376.

VT/VF detector 376 uses the ventricular rate information provided by high-rate detector 362 and interval-based metrics module 364 in combination with the SVT discriminator signal from comparator 374 for detecting VT/VF. If the SVT discriminator signal is low, VT/VF detector 376 detects SVT. If the SVT discriminator signal is high, VT/VF detector 376 detects VT or VF in accordance with the other rate and interval-based metrics available. VT/VF therapy module 378 responds to the VT or VF detection signal from VT/VF detector 376 by delivering a suitable therapy.

Thus, a system and method have been described which provide discrimination of SVT from VT/VF using ventricular EGM signals. Both high sensitivity and high specificity to VT/VF detection can be attained using comparative analysis of time-referenced monitoring EGM signals. Various embodiments of the present invention have been described in detail herein. The embodiments presented herein are intended to be exemplary, not limiting, with regard to the following claims.

What is claimed is:

1. An implantable medical device, comprising:
a first sensing device positioned at a first location to generate reference signals;
a second sensing device positioned at a second location different from the first location to generate monitoring signals timed relative to a detected fiducial point on the reference signals; and
a microprocessor identifying cardiac events in response to the reference signals and the monitoring signals, wherein the microprocessor generates a morphology metric associated with morphology differences between the monitoring signals generated during an identified cardiac event not associated with delivery of therapy and an unidentified cardiac event, and further comprising a third sensing device positioned at a third location different from the second location to generate corresponding monitoring signals timed relative to the detected fiducial point on the reference signal, wherein the morphology metric corresponds to $((1-\rho_1)\times 10)^2 + ((1-\rho_2)\times 10)^2$, wherein $\rho_1$ is a correlation coefficient associated with a monitoring signal generated by the second sensing device and $\rho_2$ is a correlation coefficient associated with a monitoring signal simultaneously generated by the third sensing device.

2. An implantable medical device, comprising:
a first sensing device positioned at a first location to generate reference signals;
a second sensing device positioned at a second location different from the first location to generate monitoring signals timed relative to a detected fiducial point on the reference signals; and
a microprocessor identifying cardiac events in response to the reference signals and the monitoring signals, wherein the microprocessor determines a first time shift and a second time shift, the first time shift being associated with a first reference signal generated by the first sensing device and a corresponding first monitoring signal substantially simultaneously generated by the second sensing device during an identified cardiac event not associated with delivery of therapy, and the second time shift being associated with a second reference signal generated by the first sensing device and a corresponding second monitoring signal substantially simultaneously generated by the second sensing device during an unidentified cardiac event.

3. The device of claim 2, wherein the microprocessor determines that the unidentified cardiac event is a cardiac event associated with delivery of therapy in response to the second time shift not being equal to the first time shift.

4. An implantable medical device, comprising:
a first sensing device positioned at a first location to generate reference signals;
a second sensing device positioned at a second location different from the first location to generate monitoring signals timed relative to a detected fiducial point on the reference signals; and
a microprocessor identifying cardiac events in response to the reference signals and the monitoring signals, wherein the microprocessor generates a morphology metric associated with morphology differences between the monitoring signals generated during an identified cardiac event not associated with delivery of therapy and an unidentified cardiac event, and further comprising a third sensing device positioned at a third location different from the second location to generate corresponding monitoring signals timed relative to the detected fiducial point on the reference signal, wherein the microprocessor determines a first time shift, a second time shift, and a third time shift, the first time shift being associated with a first reference signal generated by the first sensing device and a corresponding first monitoring signal substantially simultaneously generated by the second sensing device during an identified cardiac event not associated with delivery of therapy, the second time shift being associated with a second reference signal generated by the first sensing device and a corresponding second monitoring signal substantially simultaneously generated by the second sensing device during an unidentified cardiac event, and the third time shift being associated with the second reference signal generated by the first sensing device and a corresponding third monitoring signal substantially simultaneously generated by the third sensing device during the unidentified cardiac event, and wherein the microprocessor determines that the unidentified cardiac event is a cardiac event associated with delivery of therapy in response to one of the second time shift not being equal to the first time shift and the third time shift not being equal to a fourth time shift associated with a fourth monitoring signal substantially simultaneously generated by the third sensing device during the identified cardiac event not associated with delivery of therapy.

5. The device of claim 4, wherein the microprocessor compares a morphology of the second monitoring signal with a morphology of the first monitoring signal, compares a morphology of the third monitoring signal with a morphology of the fourth monitoring signal, and determines that the unidentified cardiac event is a cardiac event associated with delivery of therapy in response to one of the second time shift not being equal to the first time shift, the third time shift not being equal to the fourth time shift, the morphology of the second monitoring signal not being equal to the morphology of the first monitoring signal, and the morphology of the third monitoring signal not being equal to the morphology of the fourth monitoring signal.

6. An implantable medical device, comprising:
a first sensing device positioned at a first location to generate a first reference signal associated with an identified cardiac event not associated with delivery of therapy and a second reference signal associated with an unidentified cardiac event;
a second sensing device positioned at a second location different from the first location to generate a first monitoring signal timed relative to a first detected fiducial point along the first reference signal and a second monitoring signal timed relative to a second detected fiducial point along the second reference signal;
a third sensing device positioned at a third location different from the second location to generate a third monitoring signal timed relative to the second detected fiducial point and a fourth monitoring signal timed relative to the first detected fiducial point; and
a microprocessor generating a morphology metric, the morphology metric being equal to $((1-\rho_1)\times 10)^2+((1-\rho_2)\times 10)^2$, wherein $\rho_1$ is a correlation coefficient associated with the second monitoring signal and $\rho_2$ is a correlation coefficient associated with the third monitoring signal.

7. The device of claim 6, wherein the correlation coefficients $\rho_1$ and $\rho_2$ correspond to comparing a morphology of the second monitoring signal with a morphology of the first monitoring signal, comparing a morphology of the third monitoring signal with a morphology of the fourth monitoring signal, a time shift between the second monitoring signal and the first monitoring signal, and a time shift between the third monitoring signal and the fourth monitoring signal.

8. The device of claim 7, wherein the first fiducial point and the second fiducial point correspond to R-waves.

9. A method of discriminating cardiac events in an implantable medical device, comprising:
generating reference signals at a first location;
generating monitoring signals, at a second location different from the first location, timed relative to a detected fiducial point on the reference signals; and
identifying cardiac events in response to the reference signals and the monitoring signals, wherein identifying cardiac events comprises generating a morphology metric associated with morphology differences between the monitoring signals generated during an identified cardiac event not associated with delivery of therapy and an unidentified cardiac event, and further comprising generating monitoring signals, at a third location different from the second location, timed relative to the detected fiducial point on the reference signal, wherein the morphology metric corresponds to $((1-\rho_1)\times 10)^2+((1-\rho_2)\times 10)^2$, wherein $\rho_1$ is a correlation coefficient associated with a monitoring signal generated at the second location and $\rho_2$ is a correlation coefficient associated with a monitoring signal simultaneously generated at the third location.

10. A method of discriminating cardiac events in an implantable medical device, comprising:
generating reference signals at a first location;
generating monitoring signals, at a second location different from the first location, timed relative to a detected fiducial point on the reference signals; and
identifying cardiac events in response to the reference signals and the monitoring signals, wherein identifying cardiac events comprises determining a first time shift and a second time shift, the first time shift being associated with a first reference signal generated at the first location and a corresponding first monitoring signal substantially simultaneously generated at the second location during an identified cardiac event not associated with delivery of therapy, and the second time shift being associated with a second reference signal generated at the first location and a corresponding second monitoring signal substantially simultaneously generated at the second location during an unidentified cardiac event.

11. The method of claim 10, wherein the unidentified cardiac event is identified as a cardiac event associated with delivery of therapy in response to the second time shift not being equal to the first time shift.

12. A method of discriminating cardiac events in an implantable medical device, comprising:
generating reference signals at a first location;
generating monitoring signals, at a second location different from the first location, timed relative to a detected fiducial point on the reference signals; and
identifying cardiac events in response to the reference signals and the monitoring signals. wherein identifying cardiac events comprises generating a morphology metric associated with morphology differences between the monitoring signals generated during an identified cardiac event not associated with delivery of therapy and an unidentified cardiac event, and further comprising generating, at a third location different from the second location, monitoring signals timed relative to the detected fiducial point on the reference signal, wherein the microprocessor determines a first time shift, a second time shift, and a third time shift, the first time shift being associated with a first reference signal generated at the first location and a corresponding first monitoring signal substantially simultaneously generated at the second location during an identified cardiac event not associated with delivery of therapy, the second time shift being associated with a second reference signal generated at the first location and a corresponding second monitoring signal substantially simultaneously generated at the second location during an unidentified cardiac event, and the third time shift being associated with the second reference signal generated at the first location and a corresponding third monitoring signal substantially simultaneously generated at the third location during the unidentified cardiac event, and wherein the unidentified cardiac event is identified as a cardiac event associated with delivery of therapy in response to one of the second time shift not being equal to the first time shift and the third time shift not being equal to a fourth time shift associated with a fourth monitoring signal substantially simultaneously generated at the third location during the identified cardiac event not associated with delivery of therapy.

13. The device of claim 12, wherein identifying cardiac events comprises:
comparing a morphology of the second monitoring signal with a morphology of the first monitoring signal;
comparing a morphology of the third monitoring signal with a morphology of the fourth monitoring signal; and
determining that the unidentified cardiac event is a cardiac event associated with delivery of therapy in response to one of the second time shift not being equal to the first time shift, the third time shift not being equal to the fourth time shift, the morphology of the second monitoring signal not being equal to the morphology of the first monitoring signal, and the morphology of the third monitoring signal not being equal to the morphology of the fourth monitoring signal.

14. A method of discriminating cardiac events in an implantable medical device, comprising:
sensing a reference EGM signal;
setting a sensing window relative to a detected fiducial point on the reference EGM signal;
sensing a monitoring EGM signal during the sensing window during a confirmed supra-ventricular rhythm;
generating a supra-ventricular rhythm template from the monitoring EGM signal sensed during the confirmed supra-ventricular rhythm;
sensing the monitoring EGM signal during the sensing window during an unknown rhythm;
computing a morphology metric corresponding to a comparison of the supra-ventricular rhythm template to the monitoring EGM signal sensed during the sensing window during the unknown fast rhythm; and
detecting a ventricular arrhythmia if the computed morphology metric satisfies a ventricular arrhythmia detection requirement, and otherwise detecting a supra-ventricular arrhythmia if the computed morphology metric does not satisfy the ventricular arrhythmia detection requirement.

* * * * *